United States Patent [19]

Keister

[11] Patent Number: 4,870,068
[45] Date of Patent: Sep. 26, 1989

[54] METHOD OF REGULATING FERTILITY IN SWINE USING EPOSTANE

[75] Inventor: Don M. Keister, Sand Lake, N.Y.

[73] Assignee: Sterling Drug Inc., New York, N.Y.

[21] Appl. No.: 866,010

[22] Filed: May 22, 1986

[51] Int. Cl.$^4$ .............................................. A61K 31/58
[52] U.S. Cl. .................................... 514/172; 514/182; 514/874
[58] Field of Search .................... 514/172, 182, 874

[56] References Cited

U.S. PATENT DOCUMENTS

| | | | |
|---|---|---|---|
| 3,941,886 | 3/1976 | Weinshenker | 514/573 |
| 3,966,927 | 6/1976 | Binninger | 514/180 |
| 4,062,954 | 12/1977 | Potts | 514/172 |
| 4,160,027 | 7/1979 | Christiansen | 424/241 |
| 4,717,569 | 1/1988 | Harrison et al. | 514/172 |

OTHER PUBLICATIONS

Fowden et al., J. Reprod. Fert. Suppl. 35(1987) 539–545.

1986 USAN and the USP dictionary of drug names, 1961–1985 cumulative list, title page and p. 126.

Ledger et al., Journal of Steroid Biochemistry, vol. 17, No. 3, p. xci, abst. 271, 1982.

Blackwell master of science degree thesis at New Mexico State University, Las Cruces, New Mexico, 1984; title page, pp. i-xii and pp. 1–48.

Ledger et al., Journal of Endocrinology, vol. 105, pp. 227–233, 1985.

Webb, Arthur Walpole Memorial Lecture for the Society for the Study of Fertility, University of Aberdeen, 1985, pp. 1–11 and 2 fig.

*Primary Examiner*—Cecilia Shen
*Attorney, Agent, or Firm*—Theodore C. Miller; Paul E. Dupont

[57] ABSTRACT

The method of regulating fertility in swine which comprises administering to a pregnant sow near term an amount of epostane sufficient to induce parturition of live piglets on the following day is disclosed.

9 Claims, No Drawings

METHOD OF REGULATING FERTILITY IN SWINE USING EPOSTANE

BACKGROUND OF THE INVENTION

1. Field of the Invention

The invention relates to a method of regulating fertility in swine using epostane.

2. Information Disclosure Statement

Epostane is the United States Adopted Name (1986 USAN and the USP dictionary of drug names, 1961-1985 cumulative list) for $(4\alpha,5\alpha,17\beta)$-4,5-epoxy-3,17-dihydroxy-4,17-dimethylandrost-2-ene-2-carbonitrile having the structural formula

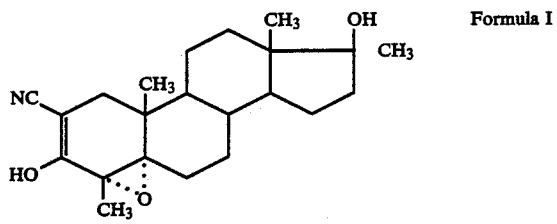

Formula I and having utility as an interceptive (pregnancy disrupting) agent.

Christiansen U.S. Pat. No. 4,160,027 issued July 3, 1979 describes epostane as the product of part (f) of EXAMPLE 1, that is, $4\alpha,5\alpha$-epoxy-$17\beta$-hydroxy-4,17-dimethyl-3-oxoandrostane-$2\alpha$-carbonitrile having the structural formula

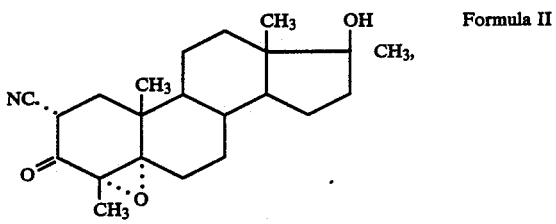

Formula II which represents the keto form of epostane. Formula I represents the enol form. The patent shows the interceptive utility of epostane in the rat and the monkey.

The only domestic animal in which the use of epostane has been described is the sheep.

A Ledger et al. (Journal of Steroid Biochemistry, vol. 17, no. 3, p. xci, abst. 271, 1982) paper entitled THE SUCCESS OF LABOUR INDUCED BY PROGESTERONE WITHDRAWAL IN PREGNANT SHEEP describes the use of epostane "to induce labour in sheep during late pregnancy".

The master of science in animal science degree thesis of Jeffrey A. Blackwell (New Mexicon State University, Las Cruces, N. Mex., 1984) entitled REPRODUCTIVE PERFORMANCE OF EWES TREATED WITH AN INHIBITOR OF PROGESTERONE SYNTHESIS describes the effects of epostane medication at day 10 of the estrus cycle in cycling ewes, specifically, serum progesterone levels, recycling time, conception rate and number of lambs produced.

A second Ledger et al. paper (Journal of Endocrinology, vol. 105, pp. 227-233, 1985) describes the "effects of an inhibitor of $3\beta$-hydroxysteroid dehydrogenase (epostane) on uterine activity and cervical softening . . . in eight sheep during late pregnancy".

The Arthur Walpole Memorial Lecture for the Society for the Study of Fertility by Robert Webb (University of Aberdeen, 1985) describes the effects of epostane on ovulation rate and production of lambs in ewes.

SUMMARY OF THE INVENTION

The invention is the method of regulating fertility in swine which comprises administering to a pregnant sow near term an amount of epostane sufficient to induce parturition of live piglets within about 24 to 48 hours postmedication.

DETAILED DESCRIPTION OF THE INVENTION INCLUSIVE OF THE PREFERRED EMBODIMENTS

In order to reduce costs in raising swine there is a need to control farrowing so that it occurs simultaneously in two or more sows. The presently described and claimed invention fulfills that need.

The normal gestation period in the pig is 115 days in length "[N]ear term" means from about day 109 onward in the gestation period. A goal of parturition induction is that all of the piglets be delivered during daylight working hours. Accordingly, "within about 24 to 48 hours postmedication" ideally means during daylight working hours on the day following epostane administration. In practice, however, farrowing might extend beyond daylight working hours and even into the second day following epostane administration, depending on the time of epostane administration and the time of onset and duration of farrowing.

Any amount of epostane sufficient to induce parturition can be used. The preferred dose is a single dose from about 1 mg./kg. to about 20 mg./kg. A second dose can be administered if farrowing does not appear imminent at 24 hr. after the first dose. The epostane can be prepared for administration in any pharmaceutically acceptable oral, vaginal, rectal or parenteral dosage form. The oral dosage form can be solid or liquid and can be capsule, tablet, solution, suspension or emulsion. The vaginal or rectal dosage form is preferably the suppository. The parenteral dosage form can be solution, suspension or emulsion. An oral or parenteral dosage form is preferred. The preferred parenteral route is subcutaneous.

The invention was carried out using twenty-five first or second liter sows divided into five groups of five. Two groups of five were treated orally with epostane (50% by weight in inert ingredients), one at 5 mg./kg. (treatment group O-5), the other at 10 mg./kg. (treatment group O-10). Two other groups of five were treated by subcutaneous injection of epostane (125 mg./ml. of a suspension in sesame oil), one at 1 mg./kg. (treatment group I-1) the other at 5 mg./kg. (treatment group I-5). Three of the remaining group of five were injected with the sesame oil vehicle only, two were untreated, and this group of five served as controls (treatment group C). Blood samples were taken at 8 a.m. on days 108 and 109 by cannulation of the vena cava. Medication was given after the blood sampling on day 109. Further blood samples were taken at 4, 8 and 12 hours postmedication, every 24 hours thereafter until onset of farrowing, and 12-24 hours postpartum.

The blood samples taken on day 109 and postpartum (and for the control group the 24-hour postmedication samples) were analyzed for packed cell volume, white blood cell count, blood urea nitrogen, sodium ion, potassium ion, chloride ion, alkaline phosphatase activity, glutamic pyruvate transaminase activity and glutamic oxaloacetic transaminase activity. None of these parameters was significantly affected by the medication.

Sows were monitored daily from day 109 until 24 hours postpartum for feed consumption, fecal consistency, body temperature and attitude. None of these parameters showed any abnormality.

For each sow the interval from treatment to onset of farrowing, that is, birth of the first piglet, and the interval from weaning until first estrus were determined. The mean intervals from treatment to onset of farrowing and durations of farrowing and standard deviations thereof were calculated. These results are set forth in Table 1.

TABLE 1

Effect of Epostane on Interval from Treatment to Onset of Farrowing and Duration of Farrowing

| Treatment Group | Mean Interval in Hours from Treatment to Onset of Farrowing ± Standard Deviation | Mean Duration in Hours of Farrowing ± Standard Deviation |
|---|---|---|
| C | 112.2 ± 44.3 | 3.2 ± 1.7 |
| O-5 | 31.2 ± 5.1 | 4.0 ± 3.7 |
| O-10 | 33.1 ± 3.8 | 7.2 ± 4.3 |
| I-1 | 77.3 ± 47.5 | 3.2 ± 1.6 |
| I-5 | 31.6 ± 3.4 | 8.3 ± 7.6 |

The mean intervals from treatment to onset of farrowing for treatment groups O-5, O-10 and I-5 are statistically different, whereas the mean interval from treatment to onset of farrowing for treatment group I-1 is not statistically different, from that of treatment group C ($p < 0.01$). Farrowing was successfully induced in all of the sows of treatment groups O-5, O-10 and I-5 but in only two of the five sows of treatment group I-1. Accordingly the 1 mg./kg. subcutaneous dose is not effective in every instance and, thus, a higher dose might be needed to effect parturition in a particular sow. The mean durations of farrowing are not statistically different but appear to tend toward longer durations with higher doses. Considering this effect and economy of drug used the minimum dose of epostane effective in inducing parturition should not be greatly exceeded.

Table 2 shows the effect of epostane on the interval from weaning until first estrus for each sow. One sow of treatment group C died prior to first estrus. These results show that the epostane medication did not have any discernible effect on this parameter.

TABLE 2

Effect on Epostane on Interval from Weaning to First Estrus

| Treatment Group | Interval from Weaning to First Estrus in Days |
|---|---|
| C | 17, 4, 4, 22 |
| O-5 | 6, 5, 20, 5, 5 |
| O-10 | 6, 6, 28, 5, 3 |
| I-1 | 5, 30, 6, 3, 4 |
| I-5 | 8, 5, 6, 4, 7 |

Piglet survival and performance were assessed by determining for each treatment group the mean number of piglets born alive, born dead and weaned and the mean birth weight and mean weaning weight of each piglet and the standard deviations thereof. The results set forth in Table 3 show that the epostane medication did not effect any of these parameters.

TABLE 3

Effect of Epostane on Piglet Survival and Performance

| Treatment Group | Mean Number Born Alive (Standard Deviation) | Mean Number Born Dead (Standard Deviation) | Mean Number Weaned (Standard Deviation) | Birth Weight in Kg. (Standard Deviation) | Weaning Weight in Kg. (Standard Deviation) |
|---|---|---|---|---|---|
| C | 8.2 (1.6) | 2.0 (1.4) | 6.0 (2.0) | 1.4 (0.3) | 5.0 (1.2) |
| O-5 | 8.4 (1.8) | 0 (0) | 5.4 (2.9) | 1.3 (0.2) | 5.1 (0.6) |
| O-10 | 8.2 (2.7) | 1.6 (1.3) | 5.4 (1.9) | 1.2 (0.1) | 4.7 (0.4) |
| I-1 | 7.4 (3.0) | 1.6 (2.3) | 5.4 (1.8) | 1.2 (0.2) | 4.7 (0.9) |
| I-5 | 7.8 (2.6) | 0.8 (0.8) | 6.2 (1.9) | 1.4 (0.3) | 4.7 (0.8) |

The plasmas from the blood samples taken as described above were stored at −20° C. and analyzed by radioimmunoassay for progesterone, total estrogen and cortisol, the concentration of each of which was calculated as a percentage of the premedication concentration determined from the blood samples taken on days 108 and 109. The results are set forth in Tables 4–6. Table 4 shows that a progesterone concentration of about 50% by 24 hours post-medication signalled oncoming parturition in treatment groups O-5, O-10 and I-5 whereas values of about 80% in the same time period in treatment groups C and I-1 showed that parturition was not imminent. Total estrogen concentrations generally decreased during the 4–24 hour postmedication period in treatment groups O-5, O-10, I-1 and I-5 while increasing in treatment group C as shown by Table 5. No clearly defined effect of epostane on cortisol concentration can be seen from the data in Table 6.

TABLE 4

Effect of Epostane on Progesterone Concentration

| Hours Postmedication | Progesterone Concentration (%) for Treatment Groups | | | | |
| | C | O-5 | O-10 | I-1 | I-5 |
|---|---|---|---|---|---|
| 4 | 113 | 48 | 48 | 89 | 62 |
| 8 | 95 | 52 | 45 | 77 | 47 |
| 12 | 92 | 50 | 66 | 67 | 53 |
| 24 | 81 | 47 | 51 | 78 | 48 |
| 36 | | | 14 | 30 | | 16 |
| 48 | 67 | | | | 107 | |
| 72 | 94 | | | | 95 | |
| 96 | 77 | | | | 77 | |

TABLE 4-continued

Effect of Epostane on Progesterone Concentration

| Hours Postmedication | Progesterone Concentration (%) for Treatment Groups | | | | |
|---|---|---|---|---|---|
| | C | O-5 | O-10 | I-1 | I-5 |
| 120 | 44 | | | 43 | |
| 132 | 9 | | | 15 | |

TABLE 5

Effect of Epostane on Total Estrogen Concentration

| Hours Postmedication | Total Estrogen Concentration (%) for Treatment Groups | | | | |
|---|---|---|---|---|---|
| | C | O-5 | O-10 | I-1 | I-5 |
| 4 | 125 | 56 | 63 | 86 | 63 |
| 8 | 125 | 48 | 57 | 72 | 55 |
| 12 | 126 | 51 | 57 | 73 | 62 |
| 24 | 142 | 127 | 67 | 80 | 67 |
| 36 | | 8 | 10 | | 8 |
| 48 | 158 | | | 100 | |
| 72 | 200 | | | 114 | |
| 96 | 184 | | | 122 | |
| 120 | 150 | | | 80 | |
| 132 | 13 | | | 15 | |

TABLE 6

Effect of Epostane on Cortisol Concentration

| Hours Postmedication | Cortisol Concentration (%) for Treatment Group | | | | |
|---|---|---|---|---|---|
| | C | O-5 | O-10 | I-1 | I-5 |
| 4 | 56 | 47 | 40 | 165 | 90 |
| 8 | 55 | 65 | 15 | 175 | 66 |
| 12 | 40 | 100 | 23 | 141 | 106 |
| 24 | 52 | 162 | 86 | 145 | 193 |
| 36 | | 68 | 40 | | 137 |
| 48 | 76 | | | 188 | |
| 72 | 96 | | | 90 | |
| 96 | 62 | | | 90 | |
| 120 | 77 | | | 218 | |
| 132 | 98 | | | 60 | |

I claim:

1. The methiod of regulating fertility in swine which comprises administering to a pregnant sow near term an amount of epostane sufficient to induce parturition of live piglets within about 24 to 48 hours postmedication.

2. The method according to claim 1 wherein the dose of epostane is from about 1 mg./kg. to about 20 mg./kg.

3. The method according to claim 2 wherein the dose of epostane is a single dose.

4. The method according to claim 3 wherein the epostane is administered orally.

5. The method according to claim 4 wherein the dose of epostane is from about 5 mg./kg. to about 10 mg./kg.

6. The method according to claim 5 wherein the dose of epostane is about 5 mg./kg.

7. The method according to claim 3 wherein the epostane is administered subcutaneously.

8. The method according to claim 7 wherein the dose of epostane is from about 5 mg./kg. to about 10 mg./kg.

9. The method according to claim 8 wherein the dose of epostane is about 5 mg./kg.

* * * * *